United States Patent
Perusse et al.

(10) Patent No.: US 9,956,154 B2
(45) Date of Patent: May 1, 2018

(54) EMULSIFYING COMPOSITION WITH CATIONIC NATURE

(71) Applicants: Centre National de la Recherche Scientifique—CNRS, Paris (FR); École Nationale Supérieure de Chimie de Rennes, Rennes (FR)

(72) Inventors: Dimitri Perusse, Rennes (FR); Thierry Benvegnu, Rennes (FR); Loïc Lemiegre, Acigné (FR); Jêrome Guilbot, Castres (FR); Hervé Rolland, Castres (FR)

(73) Assignees: CENTRE NATIONAL DE LA RECHERCHE SCIENTIFIQU-CNRS, Paris (FR); ÉCOLE NATIONALE SUPÉRIEURE DE CHIMIE DE RENNES, Rennes (FR)

( * ) Notice: Subject to any disclaimer, the term of this patent is extended or adjusted under 35 U.S.C. 154(b) by 0 days. days.

(21) Appl. No.: 15/100,155

(22) PCT Filed: Nov. 26, 2014

(86) PCT No.: PCT/EP2014/075617
§ 371 (c)(1),
(2) Date: Dec. 19, 2016

(87) PCT Pub. No.: WO2015/078890
PCT Pub. Date: Jun. 4, 2015

(65) Prior Publication Data
US 2017/0087074 A1    Mar. 30, 2017

(30) Foreign Application Priority Data

Nov. 28, 2013 (FR) ...................... 13 61770

(51) Int. Cl.
*A61K 8/44* (2006.01)
*A61K 8/46* (2006.01)
(Continued)

(52) U.S. Cl.
CPC .............. *A61K 8/447* (2013.01); *A61K 8/062* (2013.01); *A61K 8/34* (2013.01); *A61K 8/342* (2013.01);
(Continued)

(58) Field of Classification Search
CPC .... A61K 8/447; A61K 2800/591; A61Q 5/12; A61Q 1/02; A61Q 19/007
See application file for complete search history.

(56) References Cited

U.S. PATENT DOCUMENTS 6,384,266 B1    5/2002    Farone et al.

FOREIGN PATENT DOCUMENTS

EP    0770382 A1    5/1997
EP    1069142 A1    1/2001
(Continued)

OTHER PUBLICATIONS

International Search Report dated Feb. 10, 2015 re: Application No. PCT/EP2014/075617; pp. 1-3; citing: WO 2005/121294 A1, WO 2005/121291 A1, Verenikina et al. "Pangamic Acid . . . ", EP 0 770 382 A1, U.S. Pat. No. 6,384,266 B1, Maiju "Glycinebetaine".

(Continued)

*Primary Examiner* — Yanzhi Zhang
(74) *Attorney, Agent, or Firm* — Cantor Colburn LLP

(57) ABSTRACT

The invention relates to a surfactant composition including at least one compound of formula (I): in which each of the radicals Z is a hydrogen atom or ($Z_1$); at least one compound of formula (IV); one compound of formula (V); and one compound of formula (VI). The invention also relates to a method for preparing said composition and to the use thereof in cosmetics.

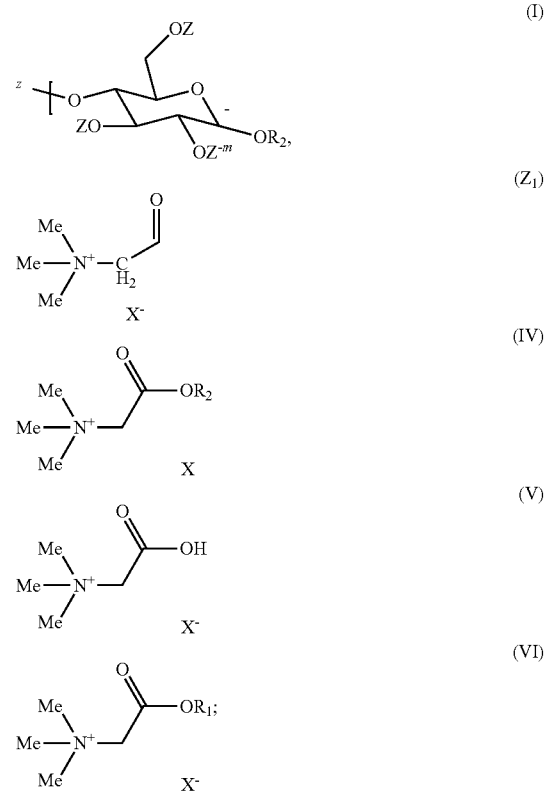

19 Claims, No Drawings

(51) Int. Cl.
*A61K 8/34* (2006.01)
*A61K 8/60* (2006.01)
*A61K 8/06* (2006.01)
*A61Q 5/12* (2006.01)
*A61Q 1/02* (2006.01)
*A61Q 19/00* (2006.01)
*A61Q 5/06* (2006.01)

(52) U.S. Cl.
CPC .............. *A61K 8/466* (2013.01); *A61K 8/602* (2013.01); *A61Q 1/02* (2013.01); *A61Q 5/06* (2013.01); *A61Q 5/12* (2013.01); *A61Q 19/007* (2013.01); *A61K 2800/49* (2013.01); *A61K 2800/591* (2013.01)

(56) References Cited

FOREIGN PATENT DOCUMENTS

| FR | 2910899 | A1 | 7/2008 | |
|----|---------|-----|---------|---|
| WO | 0244267 | A2 | 6/2002 | |
| WO | 2005012152 | A2 | 2/2005 | |
| WO | 2005121291 | A1 | 12/2005 | |
| WO | 2005121294 | A1 * | 12/2005 | ............ A61K 8/604 |
| WO | 2005121294 | A1 | 12/2005 | |
| WO | 2011030044 | A1 | 3/2011 | |

OTHER PUBLICATIONS

Maiju Korteniemi "A Short Description of Glycinebetaine (Bluestim)", Nov. 27, 2007; pp. 1-4; url:htt:/fwww.ams.usda.gov/AMSv1.0/getfile?dDocName=STELPRDC5065028; XP055143481.

S. G. Verenikina et al. "Pangamic Acid (Vitamin B15) and its derivatives", Journal of General Chemistry USSR Consultants Bureau; Jan. 1, 1967; vol. 37; pp. 2068-2181.

Ernest W. Flick, "Cosmetics additives, An industrial guide", Noyes Publications, 1991, Stephan Co. 725.

F. Nsimba Zakanda et al., "Alkylbetainate chlorides: Synthesis and behavior of monolayers at the air-water interface" Thin Solid Films, 2011, 520, 344-350.

* cited by examiner

EMULSIFYING COMPOSITION WITH CATIONIC NATURE

The invention relates to a novel surfactant composition which can be used in the preparation of cosmetic and pharmaceutical formulations having a topical use.

The use of emulsions in cosmetics or in dermopharmaceuticals is very common in the design of hygiene or care products. The formulations of this type make it possible to achieve a harmonious combination, in a homogeneous form easy to employ, of an oily phase and an aqueous phase containing ingredients of antagonistic nature, sometimes lipophilic, sometimes hydrophilic.

The emulsifying agents used under these circumstances can be of different natures. If its chemical structure concerned does not carry a charge, this compound is described as nonionic surface-active agent; if a negative charge, counterbalanced by a cation, is attached to it, it is an anionic surface-active agent; if charges of different natures coexist on the carbon-based sequence of the same chemical structure, it is an amphoteric surface-active agent; and, finally, if the chemical structure comprises a group having a positive charge counterbalanced by an anion, it is a cationic surface-active agent.

The favored ranges of applications of cationic surface-active agents are hair products and cosmetic formulations having a high presence of inorganic and/or organic fillers, such as anti-sun products. Creams, in particular those having a depilatory use, and lotions can also comprise such cationic surface-active agents.

Cationic surface-active agents of quaternary ammonium type are the most widely used in the cosmetics industry [Martin M. Reiger, "Harry's Cosmeticology", 8$^{th}$ Edition, (2000), Vol. I I-II, p. 201, Chemical Publishing]. They are in particular quaternary ammonium structures, such as trimethylstearylammonium chloride or behenyltrimonium methanesulfonate [Michael and Irene Ash, "Handbook of Lubricants", (2012), (2$^{nd}$ Edition), 999, Synapse Information Resources], sold for example by Croda under the name Incroquat Behenyl TMS [E. W. Flick, "Cosmetic and Toiletry Formulations", (1997), Vol. 6 (2$^{nd}$ Edition), 126, 210, Noyes Publications], or of trialkylbenzylammonium type, such as the benzyldimethylstearylammonium chlorides appearing in the Stepan range under the Ammonyx trade names [Ernest W. Flick, "Cosmetics additives, An industrial guide" (1991), 725, Noyes Publications].

Access to cationic surface-active agents is based very largely today on a quaternization reaction of an alkyldimethylamine with a quaternization agent capable of transferring a carbon-based group, generally a methyl radical, which reaction can be illustrated by the following scheme:

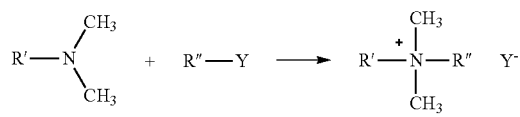

R' representing, for example, an alkyl radical comprising from 8 to 22 carbon atoms, R" representing a methyl radical or an ethyl radical and Y$^-$ representing a halide, methyl sulfate or ethyl sulfate anion.

Another approach is based on the involvement of tertiary amines of low molecular weights and of alkyl halides intended to bestow a fatty chain on the final structure and to confer surfactant properties on it. The abovementioned scheme also makes it possible to illustrate it when R' represents, for example, a methyl radical or a benzyl radical, R" represents an alkyl radical comprising from 8 to 22 carbon atoms and Y$^-$ represents a halide, methyl sulfate or tosylate anion.

In point of fact, the reactants employed according to these two approaches are of synthetic or petrochemical origin and are dangerous for the health and for the environment. This is thus particularly the case for halogenated derivatives and dimethyl and diethyl sulfates. With regard to the fatty dimethylamines, they generally originate from the conversion of fatty acids [Harold A. Wittcoff et al., "Industrial Organic Chemicals" (2004), 419, Wiley-Interscience], which also involves reactants, such as ammonia or hydrogen, which are problematic to use and which often require the presence of catalysts based on heavy metals, such as cobalt or nickel.

It has thus appeared necessary to be able to have available cationic surfactant derivatives which can be obtained from reactants not exhibiting pronounced risks for the health of man and for the environment and which can be employed under mild conditions easy to control on the industrial scale.

Glycine betaine, which is naturally present in certain fruits, such as orange or lemon, cereals, such as oats, barley or wheat, or in beet, has recently appeared as an advantageous alternative to conventional routes for achieving cationic surfactant structures [F. Nsimba Zakanda et al., "Thin Solid Films", (2011), 520, 344-350]. This is because this compound structurally carries a positive charge and makes it possible to transfer, under suitable conditions, this cationic nature to the structure to which it is chemically bonded. Glycine betaine is extracted from beet molasses, of which it represents approximately 27% by weight.

The international application published under the number WO 2005/121294 discloses novel compositions describing mixtures of alkyl hexosides or of alkyl xylosides and of fatty esters or amides of glycine betaine which can be used in bactericidal, fungicidal or preserving compositions.

The international application published under the number WO 2005/121252 discloses the use of glycine betaine derivatives in cold bituminous emulsions and mentions the preparation of glycine betaine esters or amides.

The international application published under the number WO 2005/121291 discloses the use of glycine betaine derivatives in cosmetic emulsions.

The present invention relates to novel compositions which combine glycine betaine fatty esters and esters of glycine betaine and of alkyl polyglucosides, which include in particular structures of alkyl polyglucosides type carrying a cationic group introduced by virtue of a controlled grafting of glycine betaine.

This is why, according to a first aspect, a subject matter of the invention is a composition (C$_1$) comprising, per 100 mol %:

(a)—from 0.1 mol % to 5 mol % either of a compound of formula (I):

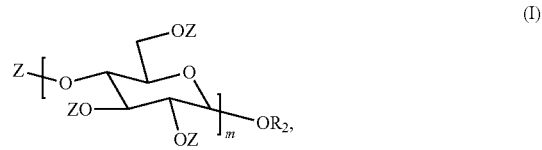

in which formula (I) each of the Z radicals represents, independently of one another, a hydrogen atom or a monovalent radical ($Z_1$):

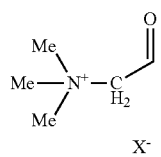

in which the $X^-$ anion represents an anion chosen from the bromide ion, the chloride ion, the iodide ion, the para-toluenesulfonate ion, the methanesulfonate ion or the trifluoromethanesulfonate ion; it being understood that at least one of the Z radicals does not represent a hydrogen atom; in which formula (I) the $R_2$ radical represents a linear or branched alkyl radical comprising from 8 to 22 carbon atoms and in which formula (I) m represents a number greater than or equal to 1 and less than or equal to 5; or of a mixture of compounds represented by said formula (I);

(b)—from 30 mol % to 60 mol % and more particularly from 50 mol % to 60 mol % either of a compound of formula (IV):

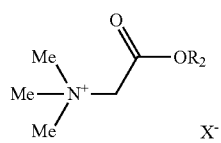

in which formula (IV) the $X^-$ anion is as defined for said radical ($Z_1$) and the $R_2$ radical is as defined for said formula (I); or of a mixture of compounds represented by said formula (IV);

(c)—from 5 mol % to 15 mol % and more particularly from 10 mol % to 15 mol % of a compound of formula (V):

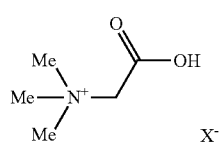

in which formula (V) the $X^-$ anion is as defined for said radical ($Z_1$);

(d)—from 15 mol % to 30 mol % and more particularly from 20 mol % to 30 mol % of a compound of formula (VI):

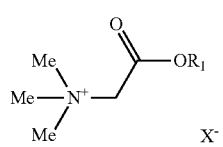

in which formula (VI) the $X^-$ anion is as defined for said radical ($Z_1$) and the $R_1$ radical represents a linear or branched alkyl radical comprising from 1 to 6 carbon atoms.

In the definition of the composition ($C_1$) which is a subject matter of the present invention, a mixture of compounds represented by said formula (I), mainly denotes a mixture of two or more compounds represented by the formulae (Ia), (Ib), (Ic), (Id) and (Ie):

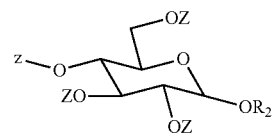

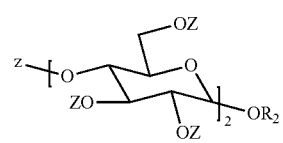

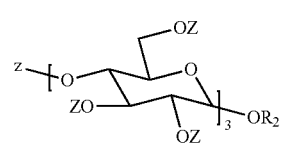

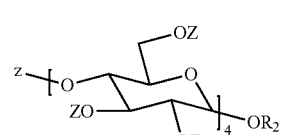

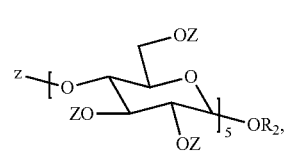

in the respective molar proportions $a_a$, $a_b$, $a_c$, $a_d$ and $a_e$, such that the sum $a_a+a_b+a_c+a_d+a_e$ is equal to 1 and that each of the proportions $a_a$, $a_b$, $a_c$, $a_d$ and $a_e$ is greater than or equal to zero and less than or equal to one.

According to a specific aspect of the present invention, the composition ($C_1$) as defined above additionally comprises, per 100 mol %:

(e)—from 5 mol % to 15 mol % either of an alcohol of formula (II):

$$R_2-OH \qquad (II)$$

in which formula (II) the $R_2$ radical represents a linear or branched alkyl radical comprising from 8 to 22 carbon atoms; or of a mixture of alcohols represented by said formula (II).

According to another specific aspect of the present invention, the composition ($C_1$) as defined above additionally comprises, per 100 mol %:

(f)—from 20 mol % to 35 mol % of a strong acid of formula (IX):

$$HX \qquad (IX)$$

chosen from hydrobromic, hydrochloric, hydriodic, para-toluenesulfonic, methanesulfonic or trifluoromethanesulfonic acid.

According to another specific aspect of the present invention, the composition ($C_1$) as defined above additionally comprises, per 100 mol %:

(g)—from 0.1 mol % to 1.5 mol % either of a compound of formula (III):

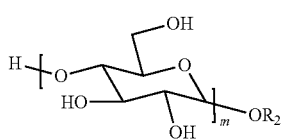

(III)

in which formula (III) the $R_2$ radical represents a linear or branched alkyl radical comprising from 8 to 22 carbon atoms; or of a mixture of compounds represented by said formula (III).

In the definition of the composition ($C_1$) which is a subject matter of the present invention, a mixture of compounds represented by said formula (III), mainly denotes a mixture of two or more compounds represented by the formulae (IIIa), (IIIb), (IIIc), (IIId) and (IIIe):

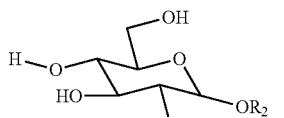

(IIIa)

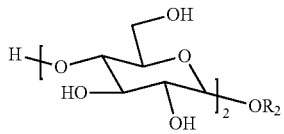

(IIIb)

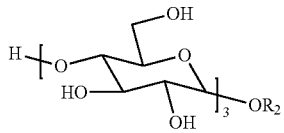

(IIIc)

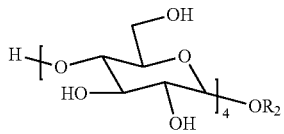

(IIId)

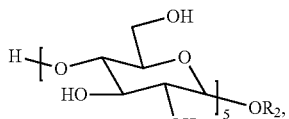

(IIIe)

in the respective molar proportions $a_a$, $a_b$, $a_c$, $a_d$ and $a_e$, such that the sum $a_a+a_b+a_c+a_d+a_e$ is equal to 1 and that each of the proportions $a_a$, $a_b$, $a_c$, $a_d$ and $a_e$ is greater than or equal to zero and less than or equal to one.

According to another specific aspect of the present invention, the composition ($C_1$) as defined above additionally comprises, per 100 mol %, from 1 mol % to 5 mol % either of a compound of formula (I), or of a mixture of compounds represented by said formula (I).

According to another specific aspect of the present invention, the composition ($C_1$) as defined above, additionally comprises, per 100 mol %:

(h)—from 0.1 mol % to 10 mol % and more particularly from 1 mol % to 5 mol % of a compound of formula (XI):

$$R_1\text{—OH} \quad \text{(XI)},$$

in which formula (XI) the $R_1$ radical represents a linear or branched alkyl radical comprising from 1 to 6 carbon atoms.

According to another specific aspect of the present invention, the composition ($C_1$) as defined above is characterized in that, in the formulae (I), (II), (III) and (IV), the $R_2$ radical is linear and is chosen from the tetradecyl, hexadecyl, octadecyl, eicosyl or docosyl radicals.

According to another specific aspect of the present invention, the composition ($C_1$) as defined above is characterized in that, in the formulae (VI) and (XI), the $R_1$ radical is the butyl radical.

According to another specific aspect of the present invention, the composition ($C_1$) as defined above is characterized in that, in the formulae (I), (IV), (V) and (VI), the $X^-$ ion represents the methanesulfonate anion and the acid of formula (IX) is methanesulfonic acid.

According to another specific aspect of the present invention, the composition ($C_1$) as defined above is characterized in that, in the formulae (I) and (III), m is equal to 1.

According to another specific aspect of the present invention, the composition ($C_1$) as defined above is characterized in that, in the formulae (I) and (III), m is greater than 1 and less than or equal to 2.5.

A subject matter of the invention is very particularly a composition ($C_1$) as defined above comprising, per 100 mol %:

(a)—from 1 mol % to 5 mol % of a compound of formula (I) or a mixture of compounds of formula (I);

(b)—from 30 mol % to 35 mol % of a compound of formula (IV) or of a mixture of compounds represented by said formula (IV);

(c)—from 8 mol % to 10 mol % of a compound of formula (V);

(d)—from 15 mol % to 20 mol % of a compound of formula (VI);

(e)—from 5 mol % to 10 mol % of an alcohol of formula (II) or of a mixture of alcohols represented by said formula (II);

(f)—from 25 mol % to 30 mol % of a strong acid of formula (IX); and (g)—from 0.5 mol % to 1.0 mol % of a compound of formula (III) or of a mixture of compounds represented by said formula (III), and optionally, (h)—from 1 mol % to 5 mol % of a compound of formula (XI).

Another subject matter of the invention is a process for the preparation of a composition ($C_1$) as defined above, characterized in that it comprises the following successive stages:

a stage a), during which 2-trimethylammonioacetate of formula (X):

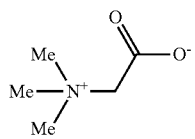

(X)

is esterified with an excess of primary alcohol of formula (XI) as defined above, in the presence of an excess of strong acid of formula (IX) as defined above, in order to form a mixture ($M_1$) comprising the compounds of formula (VI) and of formula (V), the excess alcohol of formula (XI) and the excess acid of formula (IX);

a stage b), during which said mixture ($M_1$) obtained in the preceding stage a) is reacted, in the presence of a neutralizing agent, with a mixture ($M_2$) comprising, per 100 mol %:

from 5 mol % to 20 mol % either of a compound of formula (III), or of a mixture of compounds represented by said formula (III); and from 80 mol % to 95 mol % either of an alcohol of formula (II), or of a mixture of alcohols represented by said formula (II);

in order to form a mixture ($M_3$) comprising:

the compound of formula (I) or a mixture of compounds represented by said formula (I);

the compound of formula (IV) or a mixture of compounds represented by said formula (IV);

the compound of formula (V);

the compound of formula (VI); and optionally a proportion of the alcohol of formula (II) or of a mixture of alcohols represented by said formula (II) which has not reacted, and/or the excess acid of formula (IX) and/or its salts and/or a proportion of the compound of formula (III), or of a mixture of compounds represented by said formula (III) which has not reacted and/or the compound of formula (XI) which has not reacted; and, if necessary or if desired:

a stage c), of acidification of said mixture ($M_3$) obtained in stage b), in order to obtain said composition ($C_1$).

In stage a) of the process as defined above, the use of the strong acid of formula (IX) has the role of converting the carboxylate functional group of the glycine betaine into its protenated form. It is used in a molar stoichiometric excess with respect to the glycine betaine, generally of less than or equal to 4 and in particular between 1.5 and 2.5.

In stage a) of the process as defined above, the alcohol of formula (I) is in particular employed in a stoichiometric excess of between 1.5 to 6, with respect to the glycine betaine, and more particularly between 3 and 5.

Stage a) of the process as defined above is carried out at a temperature generally of between 100° C. and 150° C., more particularly between 120° C. and 140° C., while maintaining a pressure between $5 \times 10^2$ Pa and $1.5 \times 10^5$ Pa.

In stage b) of the process as defined above, the neutralizing agent is more particularly chosen from sodium hydroxide, sodium carbonate or sodium hydrogencarbonate, and the reaction between said mixture ($M_1$) obtained in stage a) and said mixture ($M_2$) is carried out at a temperature between 40° C. and 100° C., more particularly between 65° C. and 95° C., while maintaining the pressure between $3 \times 10^2$ Pa and $5 \times 10^3$ Pa, for a period of time not exceeding 24 hours, generally between 10 hours and 20 hours.

Stage c) of the process as defined above is generally carried out with an ethanolic solution of the acid of formula (IX) in an effective amount. Said stage is generally terminated with a filtration phase in order to recover the filtered composition ($C_1$).

According to a specific aspect of the process as defined above, it comprises a stage b1), prior to stage b), during which the pH of said mixture ($M_1$) obtained on conclusion of stage a) is increased in order to at least partially neutralize the excess acid of formula (IX).

According to another specific aspect, the process as defined above also comprises a stage d) of removal of the compound of formula (XI) which has not reacted.

Another subject matter of the invention is the use of a composition ($C_1$), as defined above, as emulsifying agent in order to prepare emulsions intended for the cleaning of the skin, hair, scalp or mucous membranes or topical cosmetic emulsions intended for the care of the skin, hair, scalp or mucous membranes.

The expression "cleaning of the skin, hair, scalp or mucous membranes" denotes any action intended to make it possible to remove dirt present on the skin, hair, scalp or mucous membranes of human beings or animals. Examples of dirt present on the skin, hair, scalp or mucous membranes of human beings or animals are dust, earth, sebaceous secretions, sweat, dandruff, dead cells, microorganisms or various chemical substances, such as residues from compositions for making up and caring for the skin, hair, scalp or mucous membranes.

Finally, a subject matter of the invention is a cosmetic emulsion ($E_1$) intended for the cleaning of the skin, hair, scalp or mucous membranes or for the care of the skin, hair, scalp or mucous membranes comprising, as emulsifying agent, an effective amount of a composition ($C_1$), as defined above.

The term "effective amount" means an amount of emulsifying agent sufficient for the resulting emulsion not to phase separate at 25° C. after storage for one month.

In the context of the present invention, the term "effective amount of composition $C_1$" denotes from 0.5% to 10% by weight and more particularly from 1 to 5% by weight of said composition ($C_1$) per 100% by weight of said cosmetic emulsion ($E_1$).

When it is used for cosmetic purposes, namely to modify the external appearance of the skin, hair, scalp or mucous membranes, such as, for example, to prevent unsightly effects of aging or to clean, the emulsion ($E_1$) which is a subject matter of the present invention is more particularly administered topically.

The expression "topical" means that the emulsion ($E_1$) according to the invention is employed by application to the skin, hair, scalp or mucous membranes, whether a direct application or an indirect application is involved, for example when the emulsion ($E_1$) according to the invention is incorporated in a support intended to be brought into contact with the skin (paper, wipe, textile, transdermal device, and the like).

The topical emulsion ($E_1$) according to the invention can be packaged in a bottle and also in the pressurized form in an aerosol device or in a device of "pump-action spray" type, in a device equipped with an openwork wall, such as, for example, a grating, or in a device equipped with a ball applicator (roll-on).

The topical emulsion ($E_1$) according to the invention generally comprises chemical additives habitually employed in the field of formulations for topical use, in particular cosmetic, dermocosmetic, pharmaceutical or dermopharmaceutical formulations, such as foaming and/or detergent surfactants, thickening and/or gelling surfactants, thickening and/or gelling agents, stabilizing agents, film-forming compounds, solvents and cosolvents, hydrotropic agents, plasticizing agents, emulsifying and coemulsifying agents, opacifying agents, pearlescent agents, superfatting agents, sequestering agents, chelating agents, oils, waxes, antioxidants, fragrances, essential oils, preservatives, conditioning agents, deodorants, whitening agents intended for bleaching hairs and the skin, active principles intended to contribute a treating and/or protective action with regard to the skin or hair, sunscreens, pigments or inorganic fillers, particles which will provide a visual effect or which are intended for the encapsulation of active principles, exfoliating particles, texturing agents, optical brighteners or insect repellents.

Mention may be made, as examples of foaming and/or detergent surfactants which are optionally present in the topical emulsion ($E_1$) according to the invention, of cationic, amphoteric or nonionic foaming and/or detergent surfactants.

Mention may be made, among the amphoteric foaming and/or detergent surfactants which can be included in the topical emulsion ($E_1$) according to the invention, of alkyl betaines, alkyl amido betaines, sultaines, alkyl amidoalkyl sulfobetaines, imidazoline derivatives, phosphobetaines, amphopolyacetates and amphopropionates.

Mention may in particular be made, among the cationic foaming and/or detergent surfactants which can be included in the topical emulsion ($E_1$) according to the invention, of quaternary ammonium derivatives.

Mention may more particularly be made, among the nonionic foaming and/or detergent surfactants which can be included in the topical emulsion ($E_1$) according to the invention, of alkyl polyglycosides comprising a saturated or unsaturated and linear or branched aliphatic radical comprising from 8 to 16 carbon atoms, such as octyl polyglucoside, decyl polyglucoside, undecylenyl polyglucoside, dodecyl polyglucoside, tetradecyl polyglucoside, hexadecyl polyglucoside or 1-12 dodecanediyl polyglucoside; ethoxylated hydrogenated castor oil derivatives, such as the product sold under the INCI name "PEG-40 hydrogenated castor oil"; polysorbates, such as Polysorbate 20, Polysorbate 40, Polysorbate 60, Polysorbate 70, Polysorbate 80 or Polysorbate 85; coconut amides; or N-alkylamines.

Mention may be made, as examples of thickening and/or gelling surfactants optionally present in the topical emulsion ($E_1$) according to the invention, of optionally alkoxylated fatty esters of alkyl polyglycosides, such as ethoxylated esters of methyl polyglucoside, for example PEG-120 methyl glucose trioleate and PEG-120 methyl glucose dioleate, sold respectively under the names Glucamate™ LT and Glumate™ DOE120; alkoxylated fatty esters, such as PEG-150 pentaerythrityl tetrastearate, sold under the name Crothix™ DS53, or PEG-55 propylene glycol oleate, sold under the name Antil™ 141; or carbamates of polyalkylene glycols comprising fatty chains, such as, for example, PPG-14 laureth isophoryl dicarbamate, sold under the name Elfacos™ T211, or PPG-14 palmeth-60 hexyl dicarbamate, sold under the name Elfacos™ GT2125.

Mention may be made, as examples of thickening and/or gelling agents optionally present in the topical emulsion ($E_1$) according to the invention, of linear or branched or crosslinked polymers of polyelectrolyte type, such as, for example acrylic acid homopolymer, methacrylic acid homopolymer, 2-methyl-2-[(1-oxo-2-propenyl)amino-1-propanesulfonic acid (AMPS) homopolymer, copolymers of acrylic acid and AMPS, copolymers of acrylamide and AMPS, copolymers of vinylpyrrolidone and AMPS, copolymers of AMPS and 2-hydroxyethyl acrylate, copolymers of AMPS and 2-hydroxyethyl methacrylate, copolymers of AMPS and hydroxyethylacrylamide, copolymers of AMPS and N,N-dimethylacrylamide, copolymers of AMPS and tris(hydroxymethyl)acrylamidomethane (THAM), copolymers of acrylic or methacrylic acid and 2-hydroxyethyl acrylate, copolymers of acrylic or methacrylic acid and 2-hydroxyethyl methacrylate, copolymers of acrylic or methacrylic acid and hydroxyethylacrylamide, copolymers of acrylic or methacrylic acid and THAM, copolymers of acrylic or methacrylic acid and N,N-dimethylacrylamide, terpolymers of acrylic or methacrylic acid, AMPS and 2-hydroxyethyl acrylate, terpolymers of acrylic or methacrylic acid, AMPS and 2-hydroxyethyl methacrylate, terpolymers of acrylic or methacrylic acid, AMPS and THAM, terpolymers of acrylic or methacrylic acid, AMPS and N,N-dimethylacrylamide, terpolymers of acrylic or methacrylic acid, AMPS and acrylamide, copolymers of acrylic acid or methacrylic acid and alkyl acrylates, the carbon-based chain of which comprises between 4 and 30 carbon atoms and more particularly between 10 and 30 carbon atoms, copolymers of AMPS and of alkyl acrylates, the carbon-based chain of which comprises between 4 and 30 carbon atoms and more particularly between 10 and 30 carbon atoms, crosslinked polymers and more particularly copolymers, terpolymers and tetrapolymers comprising AMPS and macromers, such as those described in the European patent applications published under the numbers EP 1 069 142 A1 and EP 1 339 789 A2, in the international patent application published under the number WO 2011/030044 A1 and in the French patent application published under the number 2 910 899 A1.

The linear or branched or crosslinked polymers of polyelectrolyte type optionally present in the topical emulsion ($E_1$) according to the invention can be provided in the form of a solution, of an aqueous suspension, of a water-in-oil emulsion, of an oil-in-water emulsion or of a powder. The linear or branched or crosslinked polymers of polyelectrolyte type optionally present in the topical composition according to the invention can be selected from the products sold under the names Simulgel™ EG, Simulgel™ EPG, Sepigel™ 305, Simulgel™ 600, Simulgel™ NS, Simulgel™ INS 100, Simulgel™ FL, Simulgel™ A, Simulgel™ SMS 88, Sepinov™ EMT 10, Sepiplus™ 400, Sepiplus™ 265, Sepiplus™ S, Sepimax™ ZEN, Aristoflex™ HMB, Aristoflex™ VELVET, Aristoflex™ AVC, Aristoflex™ AVS, Novemer™ EC-1, Novemer™ EC-2, Flocare™ ET 25, Flocare™ ET 75, Flocare™ ET 26, Flocare™ ET 30, Flocare™ ET 58, Flocare™ PSD 30, Viscolam™ AT 64 or Viscolam™ AT 100.

Mention may be made, as examples of thickening and/or gelling agents optionally present in the topical emulsion ($E_1$) according to the invention, of polysaccharides composed solely of monosaccharides, such as, for example, glucans or glucose homopolymers, glucomannoglucans, xyloglycans, galactomannans, the degree of substitution (DS) of the D-galactose units on the main D-mannose chain of which is between 0 and 1, and more particularly between 1 and 0.25, such as, for example, the galactomannans originating from cassia gum (DS=⅕), locust bean gum (DS=¼), tara gum (DS=⅓), guar gum (DS=½), fenugreek gum (DS=1).

Mention may be made, as examples of thickening and/or gelling agents optionally present in the topical emulsion ($E_1$) according to the invention, of polysaccharides composed of monosaccharide derivatives, such as, for example, galactan sulfates and more particularly carrageenans and agar, uronans and more particularly algins, alginates and pectins, heteropolymers of monosaccharides and uronic acids and more particularly xanthan gum, gellan gum, gum arabic and karaya gum exudates, or glucosaminoglycans.

Mention may be made, as examples of thickening and/or gelling agents optionally present in the topical emulsion ($E_1$) according to the invention, of cellulose, cellulose derivatives, such as, for example, methylcellulose, ethylcellulose or hydroxypropyl cellulose, silicates, starch, hydrophilic starch derivatives or polyurethanes.

Mention may be made, as examples of stabilizing agents optionally present in the topical emulsion ($E_1$) according to the invention, for example, of microcrystalline waxes and more particularly ozokerite, inorganic salts, such as sodium chloride or magnesium chloride, or silicone polymers, such as polysiloxane polyalkyl polyether copolymers.

Mention may be made, as examples of solvents optionally present in the topical emulsion ($E_1$) according to the invention, of water, organic solvents, such as, for example glycerol, diglycerol, glycerol oligomers, ethylene glycol, propylene glycol, butylene glycol, 1,3-propanediol, 1,2-propanediol, hexylene glycol, diethylene glycol, xylitol, erythritol, sorbitol or water-soluble alcohols, such as ethanol, isopropanol or butanol, or mixtures of water and of said organic solvents.

Mention may be made, as examples of emulsifying surfactants optionally present in the topical emulsion ($E_1$) according to the invention, of nonionic surfactants and cationic surfactants.

Mention may be made, as examples of nonionic emulsifying surfactants optionally present in the topical emulsion ($E_1$) according to the invention, of esters of fatty acids and of sorbitol, such as, for example, the products sold under the names Montane™ 40, Montane™ 60, Montane™ 70, Montane™ 80 and Montane™ 85; the compositions comprising glycerol stearate and ethoxylated stearic acid having between 5 mol and 150 mol of ethylene oxide, such as, for example, the composition comprising ethoxylated stearic acid having 135 mol of ethylene oxide and glycerol stearate sold under the name Simulsol™ 165; mannitan esters; ethoxylated mannitan esters; sucrose esters; methyl glucoside esters; alkyl polyglycosides comprising a saturated or unsaturated and linear or branched aliphatic radical comprising from 14 to 36 carbon atoms, such as, for example, tetradecyl polyglucoside, hexadecyl polyglucoside, octadecyl polyglucoside, hexadecyl polyxyloside, octadecyl polyxyloside, eicosyl polyglucoside, dodecosyl polyglucoside, 2-octyldodecyl polyxyloside or 12-hydroxystearyl polyglucoside; or compositions of saturated or unsaturated and linear or branched fatty alcohols comprising from 14 to 36 carbon atoms and of alkyl polyglycosides as described above.

Mention may be made, as examples of cationic emulsifying surfactants optionally present in the topical emulsion ($E_1$) according to the invention, of amine oxides, quaternium-82, the surfactants described in the patent application WO 96/00719 and mainly those of which the fatty chain comprises at least 16 carbon atoms, or quaternary ammoniums, such as, for example, trimethylstearylammonium chloride, behenyltrimonium methanesulfonate or trialkylbenzylammoniums, such as, for example, benzyldimethylstearylammonium chlorides.

Mention may be made, as examples of opacifying and/or pearlescent agents optionally present in the topical emulsion ($E_1$) according to the invention, of sodium palmitate, sodium stearate, sodium hydroxystearate, magnesium palmitate, magnesium stearate, magnesium hydroxystearate, ethylene glycol monostearate, ethylene glycol distearate, polyethylene glycol monostearate, polyethylene glycol distearate or fatty alcohols comprising from 12 to 22 carbon atoms.

Mention may be made, as examples of texturing agents optionally present in the topical emulsion ($E_1$) according to the invention, of N-acylated derivatives of amino acids, such as, for example, the lauroyl lysine sold under the name Aminohope™ LL, the octenyl succinate starch sold under the name Dryflo™, the myristyl polyglucoside sold under the name Montanov™ 14, cellulose fibers, cotton fibers, chitosan fibers, talc, sericite or mica.

Mention may be made, as examples of deodorants optionally present in the topical emulsion ($E_1$) according to the invention, for example, of alkali metal silicates; zinc salts, such as zinc sulfate, zinc gluconate, zinc chloride, or zinc lactate; quaternary ammonium salts, such as cetyltrimethylammonium salts or cetylpyridinium salts; glycerol derivatives, such as glycerol caprate, glycerol caprylate or polyglycerol caprate; 1,2-decanediol; 1,3-propanediol; salicylic acid; sodium bicarbonate; cyclodextrins; metal zeolites; Triclosan™; aluminum bromohydrate, aluminum chlorohydrates, aluminum chloride, aluminum sulfate, aluminum zirconium chlorohydrates, aluminum zirconium trichlorohydrate, aluminum zirconium tetrachlorohydrate, aluminum zirconium pentachlorohydrate, aluminum zirconium octochlorohydrate, aluminum sulfate, sodium aluminum lactate, or complexes of aluminum chlorohydrate and of glycol, such as the aluminum chlorohydrate and propylene glycol complex, the aluminum dichlorohydrate and propylene glycol complex, the aluminum sesquichlorohydrate and propylene glycol complex, the aluminum chlorohydrate and polyethylene glycol complex, the aluminum dichlorohydrate and polyethylene glycol complex or the aluminum sesquichlorohydrate and polyethylene glycol complex.

Mention may be made, as examples of oils optionally present in the topical emulsion ($E_1$) according to the invention, of mineral oils, such as liquid paraffin, liquid petrolatum, isoparaffins or white mineral oils; oils of animal origin, such as squalene or squalane; vegetable oils, such as phytosqualane, sweet almond oil, coconut oil, castor oil, jojoba oil, olive oil, rapeseed oil, peanut oil, sunflower oil, wheatgerm oil, corn germ oil, soybean oil, cottonseed oil, alfalfa oil, poppy oil, pumpkinseed oil, evening primrose oil, millet oil, barley oil, rye oil, safflower oil, candlenut oil, passionflower oil, hazelnut oil, palm oil, shea butter, apricot kernel oil, calophylium oil, sisymbrium oil, avocado oil, calendula oil or oils resulting from flowers or vegetables; ethoxylated vegetable oils; synthetic oils, such as fatty acid esters, for example butyl myristate, propyl myristate, isopropyl myristate, cetyl myristate, isopropyl palmitate, octyl palmitate, butyl stearate, hexadecyl stearate, isopropyl stearate, octyl stearate, isocetyl stearate, dodecyl oleate, hexyl laurate, propylene glycol dicaprylate, esters derived from lanolic acid, such as isopropyl lanolate or isocetyl lanolate, fatty acid monoglycerides, diglycerides and triglycerides, such as glycerol triheptanoate, alkyl benzoates, hydrogenated oils, poly($\alpha$-olefin)s, polyolefins, such as polyisobutene, synthetic isoalkanes, such as isohexadecane or isododecane, or perfluorinated oils, or silicone oils, such as polydimethylsiloxanes, polymethylphenylsiloxanes, silicones modified by amines, silicones modified by fatty acids, silicones modified by alcohols, silicones modified by fatty acids and alcohols, silicones modified by polyether groups, epoxy-modified silicones, silicones modified by fluorinated groups, cyclic silicones and silicones modified by alkyl groups. The term "oils" is understood to mean, in the present patent application, the water-insoluble compounds and/or the mixtures of water-insoluble compounds which exist under a liquid appearance at a temperature of 25° C.

Mention may be made, as examples of waxes optionally present in the topical emulsion ($E_1$) according to the invention, of beeswax, carnauba wax, candelilla wax, ouricury wax, Japan wax, cork fiber wax, sugarcane wax, paraffin waxes, lignite waxes, microcrystalline waxes, lanolin wax, ozokerite, polyethylene wax, silicone waxes, vegetable waxes, fatty alcohols and fatty acids which are solid at ambient temperature, or glycerides which are solid at ambient temperature. The term "waxes" is understood to mean, in the present patent application, the water-insoluble compounds and/or the mixtures of water-insoluble compounds which exist under a solid appearance at a temperature of greater than or equal to 45° C.

Mention may be made, as examples of active principles optionally present in the topical emulsion ($E_1$) according to the invention, of vitamins and their derivatives, in particular their esters, such as retinol (vitamin A) and its esters (retinyl palmitate, for example), ascorbic acid (vitamin C) and its esters, sugar derivatives of ascorbic acid (such as, for example, ascorbyl glucoside) and its esters (such as, for example, tocopherol acetate), or vitamins B3 or B10 (niacinamide and its derivatives); compounds showing a lightening or depigmenting action on the skin, such as, for example, ω-undecylenoyl phenylalanine, sold under the name Sepiwhite™ MSH, Sepicalm™ VG, the glycerol monoester and/or diester of ω-undecylenoyl phenylalanine, the erythritol monoester and/or diester of ω-undecylenoyl phenylalanine, the xylitol monoester and/or diester of ω-undecylenoyl phenylalanine, the sorbitol monoester and/or diester of ω-undecylenoyl phenylalanine, ω-undecylenoyl dipeptides, such as, for example, ω-undecylenoyl-leucine-leucine, ω-undecylenoyl-isoleucine-isoleucine, ω-undecylenoyl-leucine-isoleucine or ω-undecylenoyl-isoleucine-leucine, arbutin, kojic acid or hydroquinone; compounds showing a soothing action, in particular Sepicalm™ S, allantoin and bisabolol; anti-inflammatory agents; compounds showing a moisturizing action, such as, for example, urea, hydroxyureas, glycerol, polyglycerols, glycerol glucoside, diglycerol glucoside, polyglyceryl glucosides or xylityl glucoside; plant extracts rich in polyphenols, such as, for example, grape extracts, pine extracts, wine extracts or olive extracts; compounds showing a slimming or lipolytic action, such as caffeine or its derivatives, Adiposlim™, Adipoless™ or fucoxanthin; N-acylated proteins; N-acylated peptides, such as, for example, Matrixil™; N-acylated amino acids; partial hydrolysates of N-acylated proteins; amino acids; peptides; total hydrolysates of proteins; soybean extracts, for example Raffermine™; wheat extracts, for example Tensine™ or Gliadine™; plant extracts, such as plant extracts rich in tannins, plant extracts rich in isoflavones or plant extracts rich in terpenes; extracts of freshwater or marine algae; extracts of marine plants; marine extracts in general, such as coral; essential waxes; bacterial extracts; ceramides; phospholipids; compounds showing an antimicrobial action or a purifying action, such as, for example, Lipacide™ C8G, Lipacide™ UG, Sepicontrol™ A5, Octopirox™ or Sensiva™ SC50; compounds showing an energizing or stimulating property, such as Physiogenyl™, or panthenol and its derivatives, such as Sepicap™ MP; antiaging active principles, such as Sepilift™ DPHP, Lipacide™ PVB, Sepivinol™, Sepivital™, Manoliva™, Phyto-Age™ Timecode™ or Survicode™; antiphotoaging active principles; active principles which protect the integrity of the dermoepidermal junction; active principles which increase the synthesis of the components of the extracellular matrix, such as, for example, collagen, elastins or glycosaminoglycans; active principles which act favorably on chemical cell communication, such as cytokines, or physical cell communication, such as integrins; active principles which create a feeling of "heating" on the skin, such as activators of cutaneous microcirculation (such as, for example, nicotinic acid derivatives) or products which create a feeling of "coolness" on the skin (such as, for example, menthol and derivatives); active principles which improve cutaneous microcirculation, for example venotonics, draining active principles or active principles having a decongestant purpose, such as, for example, extracts of ginkgo biloba, ivy, horse chestnut, bamboo, ruscus, butchers broom, Centalla asiatica, fucus, rosemary or willow; agents for tanning or browning the skin, such as, for example, dihydroxyacetone, isatin, alloxan, ninhydrin, glyceraldehyde, mesotartaric aldehyde, glutaraldehyde or erythrulose.

Mention may be made, as examples of sunscreens optionally present in the topical emulsion ($E_1$) according to the invention, of all those appearing in the Cosmetic Directive 76/768/EEC, amended, Annex VII.

Mention may be made, among the organic sunscreens optionally present in the topical emulsion ($E_1$) according to the invention, of the family of the benzoic acid derivatives, such as para-aminobenzoic acids (PABA), in particular monoglycerol esters of PABA, ethyl esters of N,N-dipropoxy PABA, ethyl esters of N,N-diethoxy PABA2, ethyl esters of N,N-dimethyl PABA, methyl esters of N,N-dimethyl PABA or butyl esters of N,N-dimethyl PABA; the family of the anthranilic acid derivatives, such as homomenthyl N-acetylanthranilate; the family of the salicylic acid derivatives, such as amyl salicylate, homomenthyl salicylate, ethylhexyl salicylate, phenyl salicylate, benzyl salicylate or p-isopropylphenyl salicylate; the family of the cinnamic acid derivatives, such as ethylhexyl cinnamate, ethyl 4-isopropylcinnamate, methyl 2,5-diisopropylcinnamate, propyl p-methoxycinnamate, isopropyl p-methoxycinnamate, isoamyl p-methoxycinnamate, octyl p-methoxycinnamate (2-ethylhexyl p-methoxycinnamate), 2-ethoxyethyl p-methoxycinnamate, cyclohexyl p-methoxycinnamate, ethyl α-cyano-β-phenylcinnamate, 2-ethylhexyl α-cyano-β-phenylcinnamate or mono(2-ethylhexanoyl)glyceryl di(para-methoxycinnamate); the family of the benzophenone derivatives, such as 2,4-dihydroxybenzophenone, 2,2'-dihydroxy-4-methoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl-4'-phenylbenzophenone-2-carboxylate or 2-hydroxy-4-(n-octyloxy)benzophenone or 4-hydroxy-3-carboxybenzophenone; 3-4'-methylbenzylidene-d,l-camphor 3-benzylidene-d,l-camphor, or camphor benzalkonium methosulfate; urocanic acid or ethyl urocanate; the family of the sulfonic acid derivatives, such as 2-phenylbenzimidazole-5-sulfonic acid and its salts; the family of the triazine derivatives, such as hydroxyphenyl triazine, ethylhexyloxyhydroxyphenyl-4-methoxyphenyltriazine, 2,4,6-trianilino-(p-carbo-2'-ethylhexyl-1'-oxy)-1,3,5-triazine, the 4,4-((6-(((1,1-dimethylethyl)amino)carbonyl)phenyl)amino)-1,3,5-triazine-2,4-diyl diimino) bis-(2-ethylhexyl) ester of benzoic acid, 2-phenyl-5-methylbenzoxazole, 2,2'-hydroxy-5-methylphenylbenzotriazole, 2-(2'-hydroxy-5'-(t-octyl)phenyl) benzotriazole, 2-(2'-hydroxy-5'-methyphenyl)benzotriazole; dibenzalazine; dianisoylmethane, 4-methoxy-4"-t-butyldibenzoylmethane; 5-(3,3-dimethyl-2-norbornylidene)-3-pentan-2-one; the family of the diphenylacrylate derivatives, such as 2-ethylhexyl 2-cyano-3,3-diphenyl-2-propenoate or ethyl 2-cyano-3,3-diphenyl-2-propenoate; or the family of polysiloxanes, such as benzylidene siloxane malonate.

Mention may be made, among the inorganic sunscreens, also known as "inorganic filters", optionally present in the topical emulsion ($E_1$) according to the invention, of titanium oxides, zinc oxides, cerium oxide, zirconium oxide, yellow, red or black iron oxides, or chromium oxides. These inorganic filters may or may not be micronized, may or may not have been subjected to surface treatments and may optionally be presented in the form of aqueous or oily predispersions.

The topical emulsion ($E_1$) according to the invention can more particularly be a suspension of solid particles. Said suspended solid particles present in the topical emulsion ($E_1$) according to the invention can assume different regular or irregular geometries and be provided in the form of beads, bulbs, rods, flakes, lamellae or polyhedra. These solid particles are characterized by an apparent mean diameter of between 1 micrometer and 5 millimeters, more particularly between 10 micrometers and 1 millimeter. Mention may be made, among solid particles, of micas, iron oxide, titanium oxide, zinc oxide, aluminum oxide, talc, silica, kaolin, clays, boron nitride, calcium carbonate, magnesium carbonate, magnesium hydrogencarbonate, inorganic colored pigments, polyamides, such as nylon-6, polyethylenes, polypropylenes, polystyrenes, polyesters, acrylic or methacrylic polymers, such as poly(methyl methacrylate)s, polytetrafluoroethylene, crystalline or microcrystalline waxes, porous spheres, selenium sulfide, zinc pyrithione, starches, alginates, plant fibers, loofah particles or sponge particles.

The following experimental study illustrates the invention without, however, limiting it.

EXAMPLE 1: SYNTHESIS OF THE MESYLATE OF THE BUTYL ESTER OF GLYCINE BETAINE

A suspension of 6.40 mol of glycine betaine, in 25.56 mol of butanol is prepared in a reactor. 12.80 mol of methanesulfonic acid (AMS) are then added thereto. The reaction is allowed to take place at 130° C.-140° C. After cooling at ambient temperature, 3720 g of reaction mixture ($M_1$) are obtained, which reaction mixture has the following composition (as molar percentages):
Mesylate of the butyl ester of glycine betaine [compound of formula (VI)]: 15%
Mesylate of glycine betaine [compound of formula (V)]: 4%
Methanesulfonic acid [compound of formula (IX)]: 20%
Butanol [compound of formula (XI)]: 61%

The reaction is monitored by $^1$H NMR analysis, where the deuterated mixture $CDCl_3$/MeOD (1:1 v/v) is used as solvent. Conversion of the glycine betaine observed by $^1$H NMR analysis: 80%.
Analysis
High Resolution Mass Spectrometry The mass spectrum of the compound of formula (VI) is produced using an MS/MS ZabSpec TOF Micromass® high resolution mass spectrometer. The ionization mode is positive electrospray (MS-ESI+), the voltage for acceleration of the ions is 4 kV and the temperature of the source is 60° C.

After alkaline washing of an aliquot portion of the reaction medium, butanol/ethyl acetate 4/1 (v/v) extraction and then concentration and freeze drying, the compounds are dissolved beforehand in methanol or dichloromethane.
[M]$^+$ m/z theoretical: 174, 1494; m/z found: 174, 1494 [representative of the cation $(Me)_3N^+$—$CH_2$(C=O)—O—$C_4H_9$ (MW: 174)]
Nuclear Magnetic Resonance:

The $^1$H and $^{13}$C NMR spectra of the compound of formula (VI) were respectively recorded at 400.13 MHz and 100.61 MHz on a Brucker ARX 400 spectrometer by pulsed Fourier transform (ENSCR) in tubes with a diameter of 5 mm. The chemical shifts are expressed in parts per million (ppm). The coupling constants (J) are expressed in hertz (Hz) (s=singlet, d=doublet, dd=doublet of doublets, ddd=doublet of doublet of doublets, t=triplet, at =apparent triplet, td=triplet of doublets, m=multiplet and br=nonanalyzable broad unresolved peak).

$^1$H ($CDCl_3$/MeOD 1:1 v/v; calibration with regard to deuterated methanol at 3.31 ppm; δ in ppm)
4.34 (s, 2H, $CH_2CO$);
4.24 (t, 2H, J=6.7 Hz, $CH_2O$);
3.32 (s, 9H, $(CH_3)_3N^+$);
2.71 (s, 3H, $CH_3SO_3^-$);
1.65 (m, 2H, $CH_2CH_2O$);
1.38 (m, 2H, $CH_2$);
0.93 (t, 3H, J=7.4 Hz, $CH_3$).

$^{13}$C $CDCl_3$/MeOD 1:1 v/v; calibration with regard to deuterated methanol at 49 ppm; δ in ppm)
165.32 (C=O);
66.95 ($CH_2O$);
63.54 ($CH_2N^+$);
54.23 (($CH_3)_3N^+$);
39.45 ($CH_3SO_3^-$);
30.85 ($\underline{C}H_2CH_2O$);
19.44 ($\underline{C}H_2CH_3$);
13.80 ($CH_3$).

EXAMPLE 2: PREPARATION OF A COMPOSITION ($C_1$)

The reaction medium ($M_1$) obtained in example 1 is placed in a reactor. The excess acidity is neutralized using 7.9 mole of sodium hydrogencarbonate. The mixture thus obtained is placed under reduced pressure (20 mbar). Once release of gas is no longer detected, the medium is brought back to atmospheric pressure and then 1327 g of a mixture ($M_2$) comprising 4 mol % of compound of formula (III) in which m is equal to 1.25 and $R_2$ represents a hexadecyl radical, 4 mol % of compound of formula (III) in which m is equal to 1.25 and $R_2$ represents a stearyl radical, 46 mol % of hexadecyl alcohol and 46 mol % of stearyl alcohol, and also 258 g of sodium hydrogencarbonate, are added thereto. The mixture thus obtained is again placed under reduced pressure 80° C. and 95° C. After reacting for 13 h, the mixture is cooled to approximately 50° C., the combination is brought back to atmospheric pressure and 3.5 liters of an ethanol solution comprising 472 g of MSA are added. After filtering the mixture obtained on a Büchner funnel in order to remove the residual salts, the filtrate is cooled to ambient temperature. The formation of a new precipitate is then observed, which precipitate is removed by filtration on a Büchner funnel. The new filtrate is evaporated under reduced pressure to give a yellow-colored paste.

The composition ($C_1$) is obtained, which composition comprises, as molar percentages:
Mesylate of the butyl ester of glycine betaine [Compound of formula (VI)]: 16.6%
Mesylate of glycine betaine [Compound of formula (V)]: 8.4%
Methanesulfonic acid [Compound of formula (IX)]: 27.2%
Butanol [Compound of formula (XI)]: 4.2%
Cetyl alcohol [Compound of formula (II)]: approximately 4.2 mol %
Stearyl alcohol [Compound of formula (II)]: approximately 4.2 mol %
Mesylate of the cetyl ester of glycine betaine [Compound of formula (IV)]: 16.2%
Mesylate of the stearyl ester of glycine betaine [Compound of formula (IV)]: 16.2%
Compounds of formula (I) in which $R_2$ represents a hexadecyl radical: 1.1%
Compounds of formula (I) in which $R_2$ represents a stearyl radical: 1.0%
Compounds of formula (III): 0.7 mol %.
Nuclear Magnetic Resonance:

The $^1$H NMR spectra were recorded at 400.13 MHz on a Brucker ARX 400 spectrometer by pulsed Fourier transform (ENSCR) in tubes with a diameter of 5 mm. The chemical shifts are expressed in parts per million (ppm). The coupling constants (J) are expressed in hertz (Hz) (s=singlet, d=doublet, dd=doublet of doublets, ddd=doublet of doublet of doublets, t=triplet, at =apparent triplet, td=triplet of doublets, m=multiplet and br=nonanalyzable broad unresolved peak).

NMR of the compounds of formula (IV); $^1$H CDCl$_3$/MeOD 1:1 v/v; calibration with regard to deuterated methanol at 3.31 ppm; δ in ppm)

4.34 (s, CH$_2$CO);
4.20 (t, J=6.7 Hz, CH$_2$O);
3.32 (s, (CH$_3$)$_3$N$^+$);
2.71 (s, CH$_3$SO$_3^-$);
1.71-1.58 (m, C$\underline{H}_2$CH$_2$O);
1.36-1.16 (m, (CH$_2$)$_n$);
0.83 (t, J=6.7 Hz, CH$_3$).

NMR of the fatty alcohols of formula (II); $^1$H (CDCl$_3$/MeOD 1:1 v/v; calibration with regard to deuterated methanol at 3.31 ppm; δ in ppm)

3.58 (t, J=6.8 Hz, CH$_2$OH);
2.71 (s, CH$_3$SO$_3^-$);
1.71-1.58 (m, C$\underline{H}_2$CH$_2$O);
1.36-1.16 (m, (CH$_2$)$_n$);
0.83 (t, J=6.7 Hz, CH$_3$).

NMR of the compounds of formula I with m=1; $^1$H CDCl$_3$/MeOD 1:1 v/v; calibration with regard to deuterated methanol at 3.31 ppm; δ in ppm)

4.84 (d, J=3.6 Hz, H$_1$α),
4.81 (d, J=3.6 Hz, H$_1$α),
4.74 (d, J=3.6 Hz, H$_1$),
4.37 (s, CH$_2$N$^+$), 4.04-3.38 (br, H sugars),
3.36 (s, (CH$_3$)$_3$N$^+$), 2.73 (s, CH$_3$SO$_3^-$), 1.51 (br, C$\underline{H}_2$CH$_2$O),
1.43-1.24 (br, (CH$_2$)$_n$), 0.85 (t, J=7.3 Hz, CH$_3$).

EXAMPLE 3: PREPARATION OF AN EMULSION ADVANTAGEOUS IN THE COSMETIC FIELD STARTING FROM A COMPOSITION ACCORDING TO THE INVENTION

The aqueous phase is an aliquot portion of a solution of demineralized water, the pH of which is adjusted beforehand to a value of 5.5 by virtue of controlled additions of acetic acid and sodium acetate. The fatty phase (20 g of a mixture of triglycerides of caprylic/capric type, sold by Dubois under the name Dub MCT™ 5545) and the aqueous phase (171 g) are brought beforehand separately to 80° C. The emulsifying composition (C$_1$) prepared in example 2 is dissolved with stirring in the fatty phase and then 1 g of "*Caesalpinia spinosa* gum", sold by SEPPIC under the name Solagum Tara, is introduced into the fatty phase immediately before the mixing of the two phases, which is carried out using an apparatus of rotor-stator type of the Silverson brand. The emulsion thus formed is subsequently brought back to ambient temperature under gentle stirring (150 rev/min) with a mechanical impeller of anchor type. A preservative can optionally be added during this latter phase. This type of oil-in-water emulsion remains stable in an oven at 45° C. after a period of storage of one month under these conditions.

EXAMPLE 4: PREPARATION OF AN EMULSION ADVANTAGEOUS IN THE COSMETIC FIELD STARTING FROM A COMPOSITION ACCORDING TO THE INVENTION

An emulsion like that of the preceding example 3 was prepared but without incorporating "*Caesalpinia spinosa* gum". The emulsion thus formed remains stable in an oven at 45° C. for one month.

EXAMPLE 5: FORMULATIONS

In the following formulae, the percentages are expressed as percentage by weight per 100% of the weight of the formulation.

5-1 Fluid Day Formulation

Formula

| | | |
|---|---|---|
| A | Composition (C$_1$): | 3.00% |
| | Montanov ™ 14: | 1.50% |
| | Dub ™ BB: | 2.00% |
| | *Butyrospermum parkii* (bio) | 1.50% |
| | Dub ™ MUG: | 1.50% |
| | Squalane: | 3.00% |
| | Caprylic/capric triglyceride: | 6.00% |
| | Dub ™ ISIP: | 3.00% |
| | Dermofeel TOCO 70 ™: | 0.10% |
| B | Water | q.s. for 100.00% |
| | Aqueous *Hordeum vulgare* extract | 3.50% |
| | Tara gum | 0.60% |
| C | Geogard ™ 221 | 0.60% |
| | Aquaxyl ™ | 3.00% |
| | Dermosoft ™ 700 B | 0.50% |
| | Sodium hydroxide | q.s. pH = 5.5 |

Procedure:

phase B is added to phase A at a temperature of 80° C., under stirring with a turbine of rotor/stator type, and then cooled under moderate stirring with a mechanical stirrer provided with a stirring impeller of anchor type at a rate of 80 revolutions/minute. Phase C is subsequently added under the same stirring conditions at a temperature of 40° C.

5-2 Intense Firmness Milk for the Body

Formula

| | | |
|---|---|---|
| A | Water: | q.s. for 100.00% |
| | 48% sodium hydroxide solution: | q.s. pH = 5.5 |
| | Avicel ™ PC 611: | 0.40% |
| | Glycerol: | 2.00% |
| B | Composition (C$_1$) | 2.00% |
| | Dub ™ ISIP | 4.00% |
| | Caprylic/capric triglyceride | 7.00% |
| | *Carthamus tinctorius* (safflower) oil | 1.00% |
| | Sepilift ™ DPHP | 1.00% |
| C | Aqueous *Hordeum vulgare* extract | 10.00% |
| D | Geogard ™ 221 | 0.60% |
| | Dermofeel TOCO 70 ™ | 0.10% |
| | Fragrance | 0.10% |

Procedure:

Phase A is added to phase B at 80° C. under stirring with a rotor/stator turbine. The mixture obtained is subsequently cooled to a temperature of 40° C. under moderate stirring using a mechanical stirrer provided with an impeller of anchor type at a rate of 80 revolutions/minute. Phase C is subsequently added at 40° C. and then phase D is added at 40° C.

5-3 Care Cream

| | | |
|---|---|---|
| | Cyclomethicone: | 10% |
| | Simulgel™ EG: | 0.8% |
| | Composition ($C_1$): | 2% |
| | Stearyl alcohol: | 1% |
| | Stearic alcohol: | 0.5% |
| | Preservative: | 0.65% |
| | Lysine: | 0.025% |
| | EDTA (disodium salt): | 0.05% |
| | Xanthan gum: | 0.2% |
| | Glycerol: | 3% |
| | Water: | q.s. for 100% |

5-4 Moisturizing and Mattifying Foundation

Formula

| | | |
|---|---|---|
| A | Water: | 20.0% |
| | Butylene glycol: | 4.0% |
| | PEG-400: | 4.0% |
| | Pecosil™ PS100: | 1.0% |
| | Sodium hydroxide: | q.s. pH = 9 |
| | Titanium dioxide: | 7.0% |
| | Talc: | 2.0% |
| | Yellow iron oxide: | 0.8% |
| | Red iron oxide: | 0.3% |
| | Black iron oxide: | 0.05% |
| B | Lanol™ 99: | 8% |
| | Caprylic/capric triglyceride | 8% |
| | Composition ($C_1$): | 5.00% |
| C | Water: | q.s. for 100% |
| | Micropearl™ M305: | 2.0% |
| | Tetrasodium EDTA: | 0.05% |
| D | Cyclomethicone: | 4.0% |
| | Xanthan gum: | 0.2% |
| | Simulgel™ EG: | 2.5% |
| E | Sepicide™ HB: | 0.5% |
| | Sepicide CI: | 0.3% |
| | Fragrance: | 0.2% |

Procedure

The mixtures B+D and A+C are prepared at 60° C. and then mixed, and the combination is emulsified.

5-5 Rinse-Off Hair Mask

Formula

| | | |
|---|---|---|
| A | Montanov™ 82: | 1.0% |
| | Simulsol™ 165: | 2.5% |
| | Cetearyl alcohol: | 1.5% |
| | *Argania spinosa* kernel oil | 1.0% |
| | Hydrogenated Vegetable Oil & *Prunus Amygdalus Dulcis* Oil & Tocopherol | 1.0% |
| | Mineral oil | 3.0% |
| B | Dimethicone & Dimethiconol | 3.0% |
| C | Water | q.s. for 100% |
| | Composition ($C_1$) | 3.0% |
| D | Hydroxyethylcellulose | 1.0% |
| E | Aquaxyl™ | 1.0% |
| | Phenoxyethanol & Ethylhexylglycerine | 1.0% |
| | Sepicap™ MP | 1.0% |
| | Fragrance | 1.0% |

5-6 Disentangling and Anti-Frizziness Hair Spray

Formula

| | | |
|---|---|---|
| A | Montanov™ L: | 0.5% |
| | Cyclopentasiloxane & Dimethiconol | 2.0% |
| B | Simulgel™ INS 100 | 1.2% |
| | Water | q.s. for 60% |
| C | Water | q.s. for 100% |
| | Composition ($C_1$): | 0.5% |
| D | Sepicide™ HB | 1.0% |
| | Fragrance | 0.1% |
| | Lactic acid | q.s. pH 5-5.5 |

Montanov™ 14 is a mixture of myristyl alcohol and myristyl polyglucosides sold by SEPPIC as emulsifying agent.

Dub™ BB is behenyl behenate, sold by Stéarinerie Dubois.

Dub™ MUG is glycerol undecylenate, sold by Stéarinerie Dubois.

Dub™ ISIP is isopropyl isostearate, sold by Stéarinerie Dubois.

Dermofeel TOCO 70™ is a mixture of tocopherols and *Helianthus annuus* seed oil used as an antioxidant and sold by Dr Straetmans.

Dermosoft™ 700 B: (INCI name: Levulinic acid/Sodium levulinate/Glycerine and water).

Geogard™ 221 is a mixture of dehydroacetic acid and benzyl alcohol used as preservative and sold by Lonza.

Aquaxyl™ (INCI name: Xylitylglucoside & Anhydroxylitol & Xylitol) is a composition for moisturizing and restructuring the epidermis sold by SEPPIC.

Avicel™ PC 611 is microcrystalline cellulose, sold by FMC.

Sepilift™ DPHP is DiPalmitoylHydroxyProline, sold by SEPPIC as antiwrinkle active ingredient.

Simulgel™ EG: (INCI name: Sodium acrylate/Sodium acryloyldimethyl taurate copolymer and Isohexadecane and Polysorbate 80) sold by SEPPIC;

Pecosil™ PS 100 is Dimethicone PEG-7, sold by Phoenix.

Micropearl™ M 305 is a silky water-dispersible powder based on crosslinked methyl methacrylate copolymer.

Lanol™ 99 is isononyl isononanoate, sold by SEPPIC.

Sepicide™ HB, which is a mixture of phenoxyethanol, methylparaben, ethylparaben, propylparaben and butylparaben, is a preservative sold by SEPPIC.

Sepicide™ CI, imidazolidineurea, is a preservative sold by SEPPIC.

Simulsol™ 165 is a mixture of PEG-100 stearate and glyceryl stearate.

Sepicap™ MP (INCI name: sodium cocoyl amino acids/ potassium dimethicone copolyol panthenyl phosphate).

Montanov™ 82 (INCI name: Cetearyl Alcohol (and) Coco glucoside) is a nonionic emulsifying agent sold by SEPPIC.

Montanov™ L (INCI name: $C_{14-22}$ Alcohol (and) $C_{12-20}$ Glucoside) is a nonionic emulsifying agent sold by SEPPIC.

Simulgel™ INS 100 (INCI name: Hydroxyethyl Acrylate/ Sodium Acryloyldimethyl Taurate Copolymer Isohexadecane Polysorbate 60) is a thickening agent sold by SEPPIC.

The invention claimed is:

1. A composition ($C_1$) comprising, per 100 mol %:
   (a)—from 0.1 mol % to 5 mol % either of a compound of formula (I):

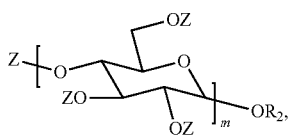
   (I)

in which formula (I) each of the Z radicals represents, independently of one another, a hydrogen atom or a monovalent radical ($Z_1$):

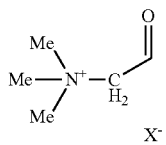
   ($Z_1$)

in which the $X^-$ anion represents an anion chosen from the bromide ion, the chloride ion, the iodide ion, the para-toluenesulfonate ion, the methanesulfonate ion or the trifluoromethanesulfonate ion; wherein at least one of the Z radicals does not represent a hydrogen atom; in which formula (I) the $R_2$ radical represents a linear or branched alkyl radical comprising from 8 to 22 carbon atoms and in which formula (I) m represents a number greater than or equal to 1 and less than or equal to 5; or of a mixture of compounds represented by said formula (I);
   (b)—from 30 mol % to 60 mol % either of a compound of formula (IV):

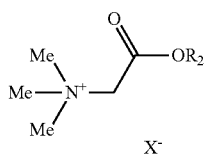
   (IV)

in which formula (IV) the $X^-$ anion is as defined for said radical ($Z_1$) and the $R_2$ radical is as defined for said formula (I); or of a mixture of compounds represented by said formula (IV);
   (c)—from 5 mol % to 15 mol % of a compound of formula (V):

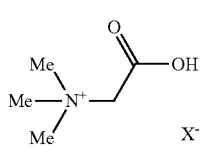
   (V)

in which formula (V) the $X^-$ anion is as defined for said radical ($Z_1$);
   (d)—from 15 mol % to 30 mol % of a compound of formula (VI):

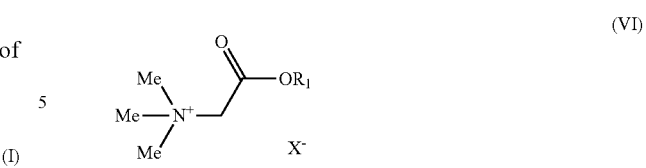
   (VI)

in which formula (VI) the $X^-$ anion is as defined for said radical ($Z_1$) and the $R_1$ radical represents a linear or branched alkyl radical comprising from 1 to 6 carbon atoms.

2. The composition ($C_1$) as defined in claim 1, additionally comprising, per 100 mol %:
   (e)—from 5 mol % to 15 mol % either of an alcohol of formula (II):

   $R_2$—OH (II)

in which formula (II) the $R_2$ radical represents a linear or branched alkyl radical comprising from 8 to 22 carbon atoms; or of a mixture of alcohols represented by said formula (II).

3. The composition ($C_1$) as defined in claim 1, additionally comprising, per 100 mol %:
   (f)—from 20 mol % to 35 mol % of a strong acid of formula (IX):

   HX (IX)

chosen from hydrobromic, hydrochloric, hydriodic, para-toluenesulfonic, methanesulfonic or trifluoromethanesulfonic acid.

4. The composition ($C_1$) as defined in claim 1, additionally comprising, per 100 mol %:
   (g)—from 0.1 mol % to 1.5 mol % either of a compound of formula (III):

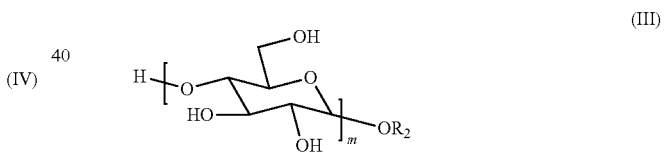
   (III)

in which formula (III) the $R_2$ radical represents a linear or branched alkyl radical comprising from 8 to 22 carbon atoms; or of a mixture of compounds represented by said formula (III).

5. The composition (CO as defined in claim 1, additionally comprising, per 100 mol %:
   (h)—from 0.1 mol % to 10 mol % of a compound of formula (XI):

   $R_1$—OH (XI), in which formula (XI) the $R_1$ radical represents a linear or branched alkyl radical comprising from 1 to 6 carbon atoms.

6. The composition ($C_1$) as defined in 5, wherein the composition comprises from 1 mol % to 5 mol % of said compound of formula (XI).

7. The composition ($C_1$) as defined in claim 1, for which, in the formulae (I), (II), (III) and (IV), the $R_2$ radical is linear and is chosen from the tetradecyl, hexadecyl, octadecyl, eicosyl or docosyl radicals.

8. The composition ($C_1$) as defined in claim 1, for which, in the formulae (VI) and (XI), the $R_1$ radical is the butyl radical.

9. The composition (CO as defined in claim 1, for which, in the formulae (I), (IV), (V) and (VI), the X⁻ ion represents the methanesulfonate anion and for which the acid of formula (IX) is methanesulfonic acid.

10. The composition ($C_1$) as defined in claim 1, for which, in the formulae (I) and (III), m is equal to 1.

11. The composition (CO as defined in claim 1, for which, in the formulae (I) and (III), m is greater than 1 and less than or equal to 2.5.

12. The composition (CO as defined in claim 1, comprising, per 100 mol %:
   (a)—from 1 mol % to 5 mol % of a compound of formula (I) or a mixture of compounds of formula (I);
   (b)—from 30 mol % to 35 mol % of a compound of formula (IV) or of a mixture of compounds represented by said formula (IV);
   (c)—from 8 mol % to 10 mol % of a compound of formula (V);
   (d)—from 15 mol % to 20 mol % of a compound of formula (VI);
   (e)—from 5 mol % to 10 mol % of an alcohol of formula (II) or of a mixture of alcohols represented by said formula (II);
   (f)—from 25 mol % to 30 mol % of a strong acid of formula (IX); and
   (g)—from 0.5 mol % to 1.0 mol % of a compound of formula (III) or of a mixture of compounds represented by said formula (III), and optionally,
   (h)—from 1 mol % to 5 mol % of a compound of formula (XI).

13. The composition ($C_1$) as defined in claim 1, wherein the composition comprises from 50 mol % to 60 mol % either of said compound of formula (IV) or of said mixture of compounds represented by said formula (IV).

14. The composition ($C_1$) as defined in claim 13, wherein the composition comprises from 10 mol % to 15 mol % of said compound of formula (V).

15. The composition ($C_1$) as defined in claim 14, wherein the composition comprises from 20 mol % to 30 mol % of said compound of formula (VI).

16. The composition ($C_1$) as defined in claim 14, additionally comprising, per 100 mol %:
   (h)—from 1 mol % to 5 mol % of a compound of formula (XI):

in which formula (XI) the $R_1$ radical represents a linear or branched alkyl radical comprising from 1 to 6 carbon atoms.

17. A process for the preparation of a composition ($C_1$) as defined in claim 1, wherein it comprises the following successive stages:
   a stage a), during which 2-trimethylammonioacetate of formula (X):

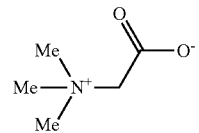

is esterified with an excess of primary alcohol of formula (XI):

in which formula (XI) the $R_1$ radical represents a linear or branched alkyl radical comprising from one to six carbon atoms, in the presence of an excess of strong acid of formula (IX):

in order to form a mixture ($M_1$) comprising the compound of formula (VI), the compound of formula (V), the excess alcohol of formula (XI) and the excess acid of formula (IX);
   a stage b), during which said mixture ($M_1$) obtained in the preceding stage a) is reacted, in the presence of a neutralizing agent, with a mixture ($M_2$) comprising, per 100 mol %:
      from 5 mol % to 20 mol % either of a compound of formula (III), or of a mixture of compounds represented by said formula (III); and
      from 80 mol % to 95 mol % either of an alcohol of formula (II), or of a mixture of alcohols represented by said formula (II);
   in order to form a mixture ($M_3$) comprising:
      the compound of formula (I) or a mixture of compounds represented by said formula (I);
      the compound of formula (IV) or a mixture of compounds represented by said formula (IV);
      the compound of formula (V);
      the compound of formula (VI); and optionally
      a proportion of the alcohol of formula (II) or of a mixture of alcohols represented by said formula (II) which has not reacted, and/or the excess acid of formula (IX) and/or its salts and/or a proportion of the compound of formula (III), or of a mixture of compounds represented by said formula (III) which has not reacted and/or the compound of formula (XI) which has not reacted; and, if necessary or if desired:
      a stage c), of acidification of said mixture ($M_3$) obtained in stage b), in order to obtain said composition ($C_1$).

18. The process as defined in claim 17, further comprising a stage b1), prior to stage b), during which the pH of said mixture ($M_1$) obtained on conclusion of stage a) is increased in order to at least partially neutralize the excess acid of formula (IX).

19. A cosmetic emulsion ($E_1$) intended for the cleaning of the skin, hair, scalp or mucous membranes or for the care of the skin, hair, scalp or mucous membranes comprising, as emulsifying agent, an effective amount of a composition ($C_1$), as defined in claim 1.

* * * * *